United States Patent [19]

Adelberger

[11] 4,253,829

[45] Mar. 3, 1981

[54] DENTAL DEVICE AND METHOD FOR REPLACING LOST TOOTH STRUCTURE

[76] Inventor: William H. Adelberger, 1375 Yellowstone Rd., Cleveland Heights, Ohio 44121

[21] Appl. No.: 13,239

[22] Filed: Feb. 21, 1979

[51] Int. Cl.³ .............................................. A61C 00/00
[52] U.S. Cl. ...................................... 433/40; 433/214
[58] Field of Search ..................... 433/218, 219, 40, 39

[56] References Cited

U.S. PATENT DOCUMENTS

| 796,120 | 8/1905 | Green | 433/39 |
| 2,958,946 | 11/1960 | Chentkof | 433/40 |
| 3,530,585 | 9/1970 | Goldstine | 633/60 |

Primary Examiner—Robert Peshock
Attorney, Agent, or Firm—Maky, Renner, Otto & Boisselle

[57] ABSTRACT

A dental device and method useful in the restoration of a tooth having extensive clinical crown loss, characterized by a multisize core form blank which may be easily and quickly sized to fit any one of a plurality of tooth sizes. The blank is in the shape of a hollow generally conical body having a converging continuous side wall defining an interior cavity for receipt of a hardenable material and is severable substantially along any one of a plurality of planes normal to the axis of the blank to produce a core form for any particular tooth size.

29 Claims, 20 Drawing Figures

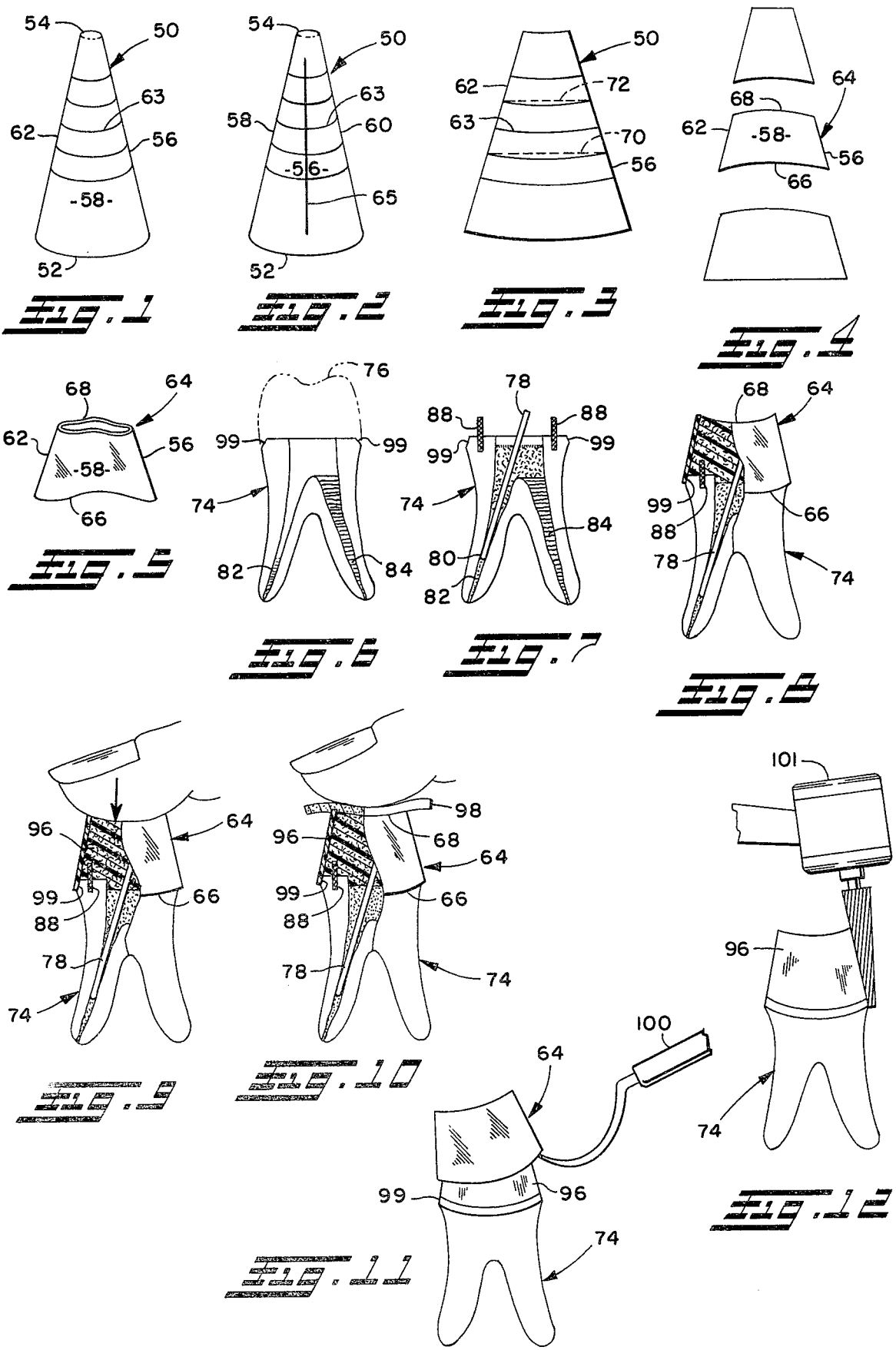

DENTAL DEVICE AND METHOD FOR REPLACING LOST TOOTH STRUCTURE

FIELD OF THE INVENTION

This invention relates to restoration and reconstruction of a deteriorated or mutilated tooth, and, more particularly, to a multisize core form blank and method useful in such work. The core form blank is particularly suited for use with composite resins and techniques employing such resins; however, such blank is also suited for use with other materials and other techniques.

BACKGROUND OF THE INVENTION

In the restoration and reconstruction of a tooth, the installation of permanent crowns is a commonplace procedure. In those cases where the tooth is not severely decayed or otherwise mutilated, the tooth may be prepared to remove the decayed or damaged portions thereof and to provide a "stump" which is adapted to receive the crown, jacket crown or cap. However, in those cases where the tooth is decayed or mutilated to such an extent that a major portion of the natural clinical crown, i.e., the portion which extends above the gum line, is lost leaving only the root structure and a portion of the clinical crown intact, the tooth cannot be prepared to provide a sufficient stump suitable to receive the crown jacket. Until recent times, the severely decayed or mutilated tooth was usually extracted and subsequently replaced with either a fixed or removable bridge as required for aesthetic and/or functional purposes.

With the advent of greater patient acceptance of root canal treatment (endodontia) and the development of new devices, materials and techniques, restoration and reconstruction of even such a badly decayed or mutilated tooth is now possible. Known restoration and reconstruction techniques generally require endodontia, the use of a post fitting within the voided root canal and a hard core integrated with the post to receive the crown. Such posts usually occupy the upper two-thirds of the canal and the core is usually located in the pulp chamber as well as in a portion of the stub of the tooth. The core, which essentially forms an artificial dentine stump, need be built only high enough to mount and reinforce the final crown, jacket crown or cap.

According to one known method for restoration and reconstruction of a badly decayed or mutilated tooth, namely the "Post and Core" method, the core is built up on a plastic or metal post with wax, drop by drop, to the approximate size of the tooth and is then shaped to the desired form with an instrument. Alternatively, the core may be built up by brushing on the post in layers an acrylic plastic which is then shaped to the desired form. In either case, the core may be built up inside the mouth directly on the prepared tooth stub (the direct technique) or outside the mouth on an impression casting (the indirect technique). Regardless of the specific procedure followed, a wax or plastic pattern results which is separated from the prepared tooth stub or impression casting. A casting is then made by the well known "lost-wax" technique to produce a cast metallic post and core which is then cemented in place into the tooth. This method, however, is extremely time-consuming for the patient and dentist and, if the direct technique is followed, uncomfortable for the patient.

Another method heretofore known, namely the "Composite Resin Build-Up" method, uses a precious or non-precious metal post cemented into the root canal, optional anchor pins screwed into the tooth stub, and a core built up on the post and pins by employing a plastic resin composition. After the root canal therapy is completed, the post, and optionally the pins, are secured in the stub. If used, the pins are normally provided with threaded or knurled surfaces adapted to interlock with the mass of air-hardenable platic resin composition retained in position against the stub by means of a core form or matrix pending hardening. Following hardening and removal of the core form, the mass of hardened resin composition is ground to the desired size and shape for receiving the final crown, jacket crown or cap.

This "Composite Resin Build-Up" method also has the drawback of being time-consuming and further requires removal of large amounts of the hardened plastic composition to produce a core of the desired size and shape as the core forms generally used today are cylindrical whereas a truncated conical core is generally preferred. Furthermore, the bulk of restorative material present as dictated by the size of the form required may be in close relationship with adjacent teeth whereby the latter may be injured unnecessarily by dental burrs or diamonds when the hardened plastic composition is being ground and shaped into the final preparation form. Moreover, a relatively large stock of forms of different sizes must be stocked by the dentist to accommodate the various tooth sizes.

One of the more common core forms employed to carry out the "Composite Resin Build-Up" method is a cylindrical copper band which is supplied in various sizes. However, such bands are not ideally suited for use in the "Composite Resin Build-Up" method in that fitting a copper band to a tooth is both difficult and time-consuming. Moreover, a very closely adapted copper band must be used in the "Composite Resin Build-Up" method because the composite resin material is relatively free flowing when initially mixed, and when placed on the tooth stub, any void between the tooth and copper band would allow the material to extrude beyond the copper band and the proposed preparation termination while held under finger pressure. Because the composite resin adheres tenaciously to natural tooth structure at times, such excess material is very undesirable since some small portions beyond the limits of the final preparation form may go undetected and later on act as a chronic irritant to the surrounding supportive tissues. Also, during the initial process of placing the composite resin filled copper band on the tooth and holding the same under firm finger pressure, because the copper band has a sleeve fit interrelationship to the remaining tooth structure, it is quite possible to over-seat the band beyond the desired point and thus cause injury to the surrounding gum tissue or to the peridontal attachment which supports the tooth. Because the copper band usually is cut by scissors at the gingival aspect thereof to mimic the cervical line of the tooth, the sharp cut edge of the band further enhances the possibility of such injury. Removal of the copper band may also be difficult and harmful to the patient as such removal is usually accomplished by cutting a continuous vertical slot through the copper band, spreading the band, grasping the band with a small forceps or similar instrument and then withdrawing the same from the tooth. During the actual removal procedure, the sharp edges of the cut copper band often cause injury to the surrounding oral tissue.

Still another known method for restoring a badly decayed or mutilated tooth utilizes a core form of transparent plastic that may be made available to the dentist in a range of sizes calculated to fit closely on the tooth stub, depending upon its size. Such form comprises a cylindrical lateral wall and an end wall fabricated of a transparent, thin, but relatively rigid, plastic material having a good memory. A form of a proper size for the tooth is located over the tooth stub and a previously positioned post and is festooned to conform to the irregular surface of the tooth stub. After being festooned, the device is inverted and filled with wax, self-curing plastic or other material and when no longer in a free flowing state, it is then forced over the tooth stub with the excess thereof being squeezed out at the lower margin of the side wall and immediately trimmed away. When the plastic material hardens, the form is cut and stripped from the core, after which the core and post pattern are separated from the stub and a casting is made by the well-known "lost-wax" technique and later cemented into the tooth stub.

OBJECTS OF THE INVENTION

In view of the foregoing, it is a principal object of this invention to provide a multisize core form blank which may readily be sized to accommodate various tooth sizes thereby eliminating the need to stock core forms of a large number of sizes.

Another principal object of the invention is to provide such a core form blank which is particularly suited for use with composite resins or acrylic plastic resins and techniques employing same.

Still another object of the invention is to provide such a core form blank which eliminates the need to remove by grinding or other means large quantities of hardened core material in order to obtain the desired final preparation form of the core.

Yet another object of the invention is to provide such a core form blank which, after sizing, will not undesirably overseat on the remaining tooth stub when subjected to firm pressure.

A further object of the invention is to provide such a core form blank that is readily adapted for use in a variety of restoration and reconstruction techniques, e.g., the "Post and Core" and "Composite Resin Build-Up" methods and variations thereof.

Still a further object of the invention is to provide such a core form blank which is readily adapted after sizing to fit closely and snugly the configuration of the remaining tooth stub.

Yet a further object of the invention is to provide a core form blank and method for forming the core on a tooth stub which is time efficient and comfortable for the patient.

Yet still a further object of the invention is to provide such a device and method which eliminates possible injury to the patient's surrounding teeth and gums during the formation of the core on a tooth stub and during removal of the core form from the tooth being reconstructed.

These and other objects of the invention will become apparent as the following description of the invention proceeds.

SUMMARY OF THE INVENTION

In contradistinction to known core forms and methods for reconstructing and restoring a tooth, the device and method of this invention are characterized by a multisize core form blank in the form of a hollow generally conical body having a thin, flexible, continuous and converging sidewall defining an interior cavity adapted to receive a hardenable material therein. The multisize core form blank is severable substantially along any one of a plurality of planes substantially normal to the long axis of the core form blank to define an open gingival aspect or base end having an interior cross-sectional shape and size adapted to surround and closely conform to the vital or non-vital tooth stub when installed.

Only one size or relatively few sizes of the multisize core form blank need be provided to accommodate the various tooth sizes as different transverse cross-sections are taken for different sizes of teeth. Moreover, the tapered sidewall limits by a binding action the movement of the "sized" core form over the tooth stub to obtain proper seating of the "sized" core form and also permits easy removal of the "sized" core form from the hardened material without the necessity of vertical slotting.

The multisize core form blank may also be severed substantially along another of a plurality of planes substantially parallel to such gingival aspect to define the height of the "sized" core form, and thus provide a "sized" core form having an interior cavity of a generally truncated conical shape. Further, the "sized" core form may be slightly embedded in an apex stop to form an occlusal wall of the cavity and to provide a handle for filling and placing the core form. Alternatively, a conical slug of a desired size may be inserted into the apex of the core form to limit the height of the interior cavity. In either case, the resulting "sized" core form thus approximates the desired truncated final form of the tooth core thus reducing substantially the amount of core material that must be removed in order to obtain such desired shape.

Two types of multisize core form blanks preferably are provided, respectively, for posterior and anterior teeth. The posterior type of multisize core form blank is substantially conical in shape with substantially a straight tapered sidewall. The core form may be open or closed at its apex and/or base, and preferably cross-sections taken normal to the apical axis of the core form are substantially circular to conform closely to the shape of a posterior tooth. The anterior type of multisize core form blank has a sidewall substantially straight along the interproximal sides thereof and slightly longitudinally convex and concave, respectively, along the facial and lingual sides. Preferably, the sidewall of such form medially along the exterior convex facial side (and/or concave lingual side) is provided with a longitudinally extending vertical limiting ridge projecting outwardly from the surface thereof to facilitate proper positioning and alignment of the "sized" core form relative to the corresponding opposing teeth in the opposing dental arch.

Although the core form blank and resulting "sized" core form of the invention is particularly suited for use with composite resins or like restorative materials, it may be used, for example, to form a post and core pattern by which the post and core are cast by the lost-wax technique. In such method, an apex stop may be provided for use with the "sized" truncated conical form, such apex stop comprising a disc having an opening therein through which the post may project beyond the form to provide a sprue for the subsequent casting process.

To the accomplishment of the foregoing and related ends, the invention, then, comprises the features hereinafter fully described and particularly pointed out in the claims, the following description and the annexed drawings setting forth in detail certain illustrative embodiments of the invention, these being indicative, however, of but a few of the various ways in which the principles of the invention may be employed.

BRIEF DESCRIPTION OF THE DRAWINGS

In the annexed drawings:

FIG. 1 is a perspective view of the posterior type of dental device according to the invention with the mesial (or distal) side thereof facing the viewer;

FIG. 2 is a perspective view of the device of FIG. 1 with the facial (or lingual) side thereof facing the viewer;

FIGS. 3-12 are views illustrating the device of FIGS. 1 and 2 as employed in carrying out the method of the invention for restoring a posterior tooth having extensive clinical crown loss in which composite resins or like restorative materials are employed to reconstruct the posterior tooth;

DESCRIPTION OF THE PREFERRED EMBODIMENTS

Figure 16:
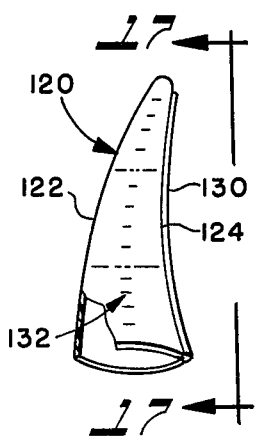
FIG. 16 is a perspective view of the anterior type of dental device according to the invention with the mesial (or distal) side thereof facing the viewer.
Figure 17:
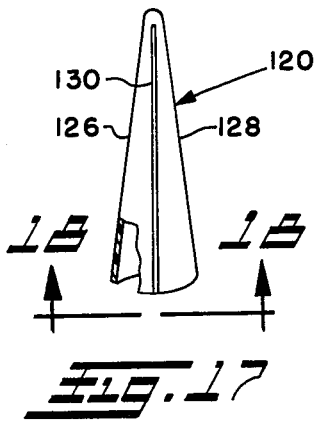
FIG. 17 is a perspective view of the device of FIG. 16 with the facial (or lingual) side thereof facing the viewer, as seen from the line 17—17 of FIG. 16.

Referring now in greater detail to the drawings, the multisize core form blank according to the present invention may take two basic configurations as seen in FIGS. 1-2 and 16-17, respectively. The configuration of FIGS. 1-2, for example, is intended for use primarily with a posterior tooth of a patient, i.e., a molar or premolar tooth, and will be termed the posterior type, whereas the configuration of FIGS. 16-17 is intended for use primarily with an anterior tooth of the patient, i.e., an incisor or canine tooth, and will be termed the anterior type. However, either type core form blank may be used with either type of tooth. The posterior type multisize core form blank and its employment in carrying out the method of the invention first will be described.

Referring initially to FIGS. 1 and 2, the posterior type multisize core form blank 50 according to the invention is in the form of a hollow conical body having a thin, flexible, continuous, straight sidewall defining an interior conical cavity. The core form blank 50 may be fabricated of a suitable flexible material such as plastic, rubber or metal and may be either transparent, translucent or opaque as desired. Moreover, the core form blank 50 preferably is open at its larger diameter or base end 52 and may either be open or closed at its apex end 54. The core form blank 50 when appropriately sized as described below is adapted to conform to a remaining tooth stub with the sidewall having a facial side 56, mesial side 58, distal side 60 and lingual side 62 corresponding generally to like sides of the tooth to be restored.

Preferred materials for the blank 50 are polypropylene and polyethylene. In addition, the blank 50 may be readily formed by conventional vacuum forming techniques.

The blank 50 may be provided with indices or other markings indicated generally by reference numeral 63 for a purpose which will become apparent below. The markings 63 may partially or totally (as shown) circumscribe the blank 50 and preferably are arranged in a suitable vertical (longitudinal) pattern. Also provided is a facial index 65 in the form of a vertical line. Because the core form blank 50 is essentially symmetrical, the facial index may be employed to define an arbitrary facial side 56.

Referring now additionally to FIGS. 3-5, the multisize core form blank 50 may be severed, such as by cutting with a suitable tool such as straight scissors, substantially along any of a plurality of planes normal to the longitudinal or apical axis of the core form to form a "sized" or "working" core form or matrix 64 seen in FIG. 5. The "sized" core form 64 essentially comprises a section of the multisize core form blank 50 and is substantially frusto-conical in shape having gingival end 66 and occlusal end 68. By taking a proper section of the multisize blank 50, a "sized" core form or matrix 64 may be formed to accommodate most tooth sizes.

The index markings 63 and facial index 65 will aid the dentist in selecting the proper cut lines for a given required section, for example, cut lines 70 and 72 which form the gingival aspect 66 and occlusal aspect 68 of the sized core form 64. The index markings 63 and facial index 65 will also aid in locating and orientating the resulting "sized" core form 64 on the tooth stub as will be better appreciated below. Although FIGS. 3 and 4 show three such sections being taken from a single blank 50, normally only one "sized" section will be used from any one multisize blank as the remaining sections likely will be unusable by the dentist and will be discarded rather than saved.

To sever the multisize core form blank 50 to obtain a desired section, the same preferably is gently squeezed longitudinally with the opposed mesial side 58 and distal side 60 thereof being urged towards one another as seen in elevation in FIG. 3. With the blank 50 so squeezed, the blank may be cut by straight scissors along previously identified cut lines 70 and 72. It should be appreciated that the blank 50 need not be completely flattened before cutting and such flattening actually would be undesirable as it would tend to crease the blank.

It will be appreciated that by gently squeezing and cutting the blank 50, the gingival aspect 66 of the resulting "sized" core form 64 will be festooned to mimic the cervical line of a tooth stub when the same is properly located on the tooth. As best seen in elevation in FIGS. 4 and 5, the mesial and distal sides 58 and 60 will be slightly concave at the gingival end 66. Accordingly, the facial and lingual sides 56 and 62 will be slightly convex at the gingival end.

In order that a "sized" core form 64 may be formed for use in restoring most tooth sizes, the multisize blank 50 may have a height of approximately 2.1 cm., a greatest inner diameter of approximately 1.2 cm. and a sidewall inclination to the apical axis of the blank of approximately 13°. In addition, the sidewall thickness is preferably on the order of about 0.025 cm. to about 0.03 cm. A multisize core form blank of such size will normally accommodate most sizes of molars and premolars, although other dimensions thereof may be provided if desired. It will also be appreciated that such size of multisize core form blank will accommodate essentially all tooth sizes previously accommodated by cylindrical copper band sizes ranging from #1 (approximately 0.45 cm. diameter) to #20 (approximately 1.2 cm. diameter).

Referring now additionally to FIGS. 6-14, the use of the above described posterior type of multisize core form blank 50 according to the method of the invention for restoration of a lower posterior tooth will be described. It, however, should be noted that the exemplary case described below for a lower posterior tooth obviously is equally applicable in the case of an upper posterior tooth, everything being inverted. Moreover, the below exemplary case will pertain principally to a method employing composite resins or like restorative materials, it also being understood that the multisize core form blank may be used with other restorative or pattern making materials and techniques.

Referring firstly to FIG. 6, a lower posterior tooth 74 with extensive clinical crown loss is seen after root canal treatment (endodontia) has been completed and the remaining tooth stub prepared to receive a core. For illustrative purposes, the normal clinical crown profile of the tooth is indicated by dashed line 76.

After initial preparation of the tooth 74, a dowel or post 78 is inserted in one of the plural canals 80 thereof as seen in FIG. 7. Preferably, the post 78 is selected overlength and then is trimmed to the desired height generally just below the estimated position of the occlusal plane of the soon-to-be fabricated core. At this stage, the patient may close his mouth to verify the height of the post, and, if necessary, the height of the post may be appropriately adjusted. Before final insertion of the post into the root canal 80, about the apical (root end) one third of such root canal will have been obturated as indicated at 82 while the other root canal may be substantially obturated as indicated at 84. Preferably, but optionally, pins 88 are secured in the stub of the tooth 74 with portions thereof projecting outwardly from the remaining tooth structure into the space to be occupied by the core to be formed. Such pins 88 may or may not be provided with knurled or threaded surfaces at their exposed ends adapted to interlock with the later formed core. Commonly, two or more such pins are provided. The tooth 74 is now ready to receive the core to be formed.

To form the core on the tooth stub 74, the multisize core form blank 50 is first sized to the tooth stub by selecting the proper cross-section of the gingival aspect 66. To facilitate such selection, the multisize blank 50 may be positioned proximate to the tooth stub 74 and an appropriate index marking 63 identified for indicating the proper cutting line. The multisize blank 50 may then be removed and the same substantially cut such as by straight scissors along a plane normal to the apical axis thereof coinciding with the noted index marking in the manner indicated above to form the gingival aspect 66. The blank then may be located on the tooth stub 74 with the gingival aspect 66 thereof conforming to the side surfaces of the tooth stub at the gum line for selection of the proper height of the same, for example, by identifying a second index marking. The blank may then be severed as described above to form the occlusal aspect 68 of the resulting properly "sized" core form 64 of the desired truncated conical shape and size as seen in FIG. 8.

The "sized" or "working" core form 64 may now be filled with a suitable restorative material such as an air-hardenable plastic resin or epoxy composition. While the composition is still in a soft state, the "sized" core form 64 is forced over and onto the prepared tooth stub 74. The "sized" core form 64 is then held under firm pressure as seen in FIG. 9 such as by placing a finger at the exposed occlusal aspect 68 thereof until the composite resin hardens forming the core 96, it being appreciated that the finger depressing the "sized" core form essentially forms the occlusal wall of the core form to define a closed core cavity.

To facilitate handling, a matrix apex stop 98 comprised of a thin flat flexible disc having a transverse dimension greater than that of the core form may be employed as seen in FIG. 10 to form the occlusal wall of the core form. Preferably, the apex stop 98 is formed of a semi-impressionable material whereby the edge of the core form 64 at the occlusal aspect thereof may be pressed slightly into and embedded in the apex stop. In this manner, the apex stop, in addition to forming the occlusal wall of the core form, provides a handle by which the core form may be manipulated during filling of the same with the hardenable material and placing of the same on the remaining tooth structure. A preferred material for the apex stop is base plate wax.

It should be appreciated that overseating of "sized" core form 64 due to the pressure applied essentially is eliminated as the converging sidewall of the core form limits its downward movement over the tooth stub. Further to facilitate proper seating, the peripheral edge of the remaining crown of the tooth 74 at the gum line may be tapered as seen at 99 in FIGS. 6-10. Such taper further provides the desired contact between a crown and the natural tooth structure which is usually on the order of 2.0 mm.

After the composite resin sets, the "sized" core form 64 may be easily separated and removed in one piece with a suitable tool 100 from the core 96 as seen in FIG. 11, as the converging sidewall thereof provides a sufficient draft angle eliminating the undesirable cutting thereof. After removal of the "sized" core form 64, the hardened core 96 may then be finish ground with a suitable tool 101 in conventional manner to the precise desired form as seen in FIG. 12 to produce a core 96 of the desired size and truncated conical shape to which a permanent crown may be fitted. Because the shape of the set composition approximates closely the final preparation form of the core, only minimal preparation or removal of excess material is required.

Figure 13:
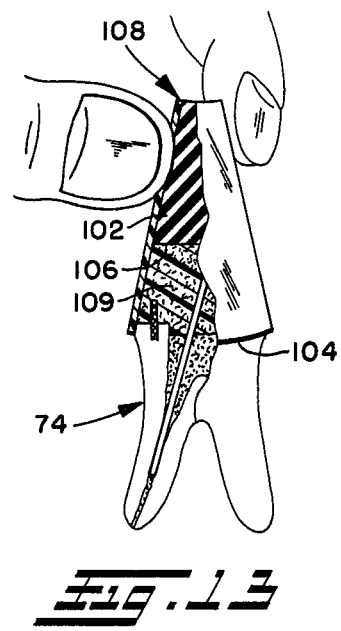
FIG. 13 is a view illustrating a variation of the method of the invention.

Referring now to FIG. 13, it will be seen that the foregoing method may be modified slightly with the employment of a solid insert slug 102 made of rubber, silicone, silicone rubber or other suitable material which is of a shape to fit within the interior cavity of the multisize core form blank at the upper or apical portion thereof. The slug 102 is sized to limit the volume of material placed in the matrix thereby to limit the height of the amount of restorative material formed upon the remaining tooth structure 74. By employing such slug, the blank is severed only to form the gingival aspect 104 and a slug 102 is inserted into the apical end of the blank to fill the same, such slug being a proper size so that the base 106 thereof is spaced from the gingival aspect 104 the desired height of the core to be formed. Preferably, a multisize slug blank is provided so that the dentist may cut the same similar to the core form blank 50 to obtain an insert slug 102 of an appropriate height. Of course, insert slugs 102 of varying heights may alternatively be provided. The resulting modified "sized" core form 108 can now be filled with restorative material and the apical portion thereof can now be used as a handle to locate the form on the tooth 74 and to apply pressure while the restorative material is undergoing set to form hardened core 109 as seen in FIG. 13.

Figure 14:
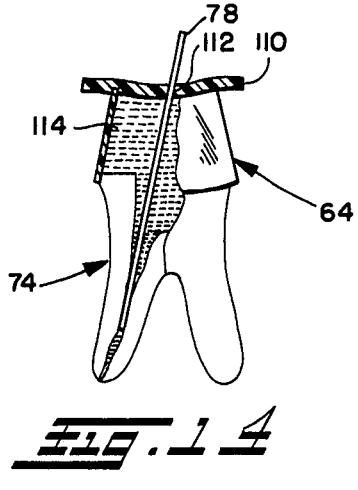
FIGS. 14 and 15 are views illustrating another variation of the method of the invention in which a core and post pattern is formed.
Figure 15:
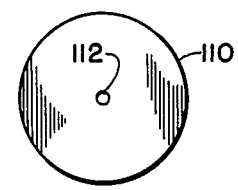

A further modification according to the invention can be seen in FIGS. 14 and 15, wherein a matrix apex stop 110 is employed along with a "sized" core form 64. The apex stop 110, which is similar to the apex stop 98, has a hole or slit 112 in its center and may be made of rubber, wax, silicone, silicone rubber or any other suitable material. The apex stop 110 may be employed whenever the dentist decides to allow the post 78 to extend above the "sized" core form 64 such as in the case where the protruding post would act as a sprue in the "lost-wax" casting technique. It will be appreciated that the post 78 will pass through the opening 112 with a close fit to prevent extrusion of moldable material therethrough.

As seen in FIG. 14, the "sized" core form 64, for example, may be filled with wax in its softened state and positioned over the prepared tooth stub 74 with the post 78 extending through the slot 112 in the apex stop 110. After the wax has hardened, the core form and apex stop may be removed along with the hardened wax pattern 114 for preparation of the cast core and post by the "lost-wax" technique which cast core and post may later be cemented in place in the tooth stub 74.

Figure 18:
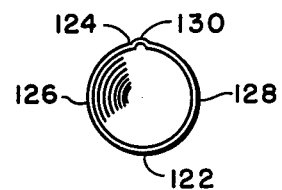
FIG. 18 is an end view of the device of FIGS. 16 and 17 as seen from the line 18—18 of FIG. 17.

Referring now to FIGS. 16–18, an anterior type multisize core form blank 120 according to the invention also can be seen to be in the shape of a hollow conical body having a thin, flexible continuous sidewall defining an interior conical cavity and is formed similar to the posterior core form blank 50 while differing in those respects as are discussed below. In contrast to the posterior type multisize core form blank 50, the anterior type has an opposed gently curving convex facial side 122 and a gently curving concave lingual side 124 with only the mesial side 126 and distal side 128 being substantially straight. Such core form blank better conforms to the shape of anterior teeth.

The blank 120 may further include a raised limiting ridge 130 extending outwardly and longitudinally the length of the same which may be located on either the facial or lingual sides for use with lower or upper tooth, respectively, or a limiting ridge may be provided on both such facial and lingual sides if desired. The limiting ridge may have a U-shape cross-section as shown in FIG. 18 or may be solid. As was the case in the posterior type blank 50, the anterior type blank 120 may be closed or opened at its base and/or apex ends, and the blank 120 also may be provided with indices or other markings indicated generally by reference numeral 132 to assist the dentist in selecting the proper planes for the gingival and occlusal ends for a particular tooth size. The markings may totally or partially circumscribe the multi-size matrix and preferably are arranged in a suitable vertical (longitudinal) pattern.

To accommodate most tooth sizes, the blank 120 may have a height of approximately 2.0 cm., a greatest inner dimension between the proximal surfaces of the matrix of approximately 0.9 cm. and a sidewall inclination at the interproximal sides of approximately 10° to the apical axis of the blank. In addition, the sidewall thickness is preferably on the order of about 0.025 cm. to about 0.03 cm. A multisize blank of such size will accommodate most sizes of anterior teeth, although other dimensions thereof may function properly.

Figure 19:
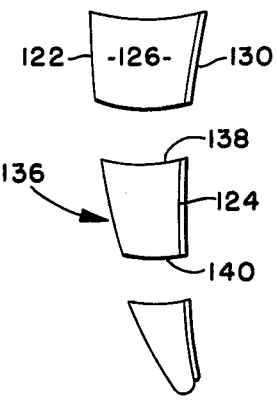
FIGS. 19 and 20 are views illustrating the device of FIGS. 16 and 17 as employed in carrying out the method of the invention for restoring an anterior tooth.
Figure 20:
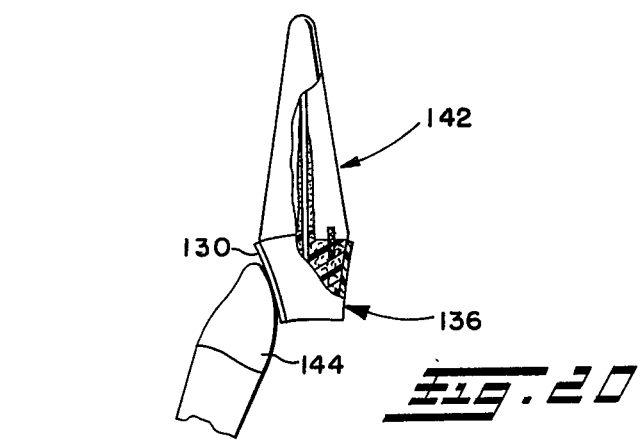

The anterior type blank 120 may be employed essentially in like manner as the posterior type blank 50 but preferably to reconstruct an anterior tooth. As seen in elevation in FIG. 19, the anterior type blank 120 can be readily sized to form a "sized" core form 136 with a contoured gingival aspect 138 and occlusal aspect 140. Such "sized" core form 136 may then be employed according to the above described method. However, it will be appreciated that when the "sized" core form 136 is placed on the remaining anterior tooth structure 142 as seen in FIG. 20, the limiting ridge 130 facilitates positioning of the core form 136 relative to an opposing tooth 144 of the opposite jaw to provide sufficient clearance for placement of a crown on the tooth being restored. Absent such limiting ridge, the dentist would have to guess as to appropriate spacing between the opposed teeth. Such limiting ridge will also provide proper spacing in the event a suitable apex stop or insert slug is employed.

Although the invention has been shown and described with respect to a certain preferred embodiment, it is obvious that equivalent alterations and modifications will occur to those skilled in the art upon the reading and understanding of the specification. The present invention includes all such equivalent alterations and modifications and is limited only by the scope of the claims.

The embodiments of the invention in which an exclusive property or privilege is claimed are defined as follows:

1. A dental core form device for the preparation of a core for a crown on a prepared remaining tooth stub having extensive clinical crown loss, said device comprising a hollow conical blank having tapered continuous sidewall means severable substantially along any one of a plurality of planes substantially normal to the apical axis of said blank to produce a core form having an open gingival aspect with a transverse cross-sectional size and shape adapted to surround and to conform to the tooth stub when installed thereon and an interior cavity adapted to receive a hardenable material and to shape such hardenable material to a desired final form, said tapered sidewall means being adapted to conform to the tooth stub and limit by a binding action the movement of the core form over the tooth stub to obtain proper seating of the core form on the tooth stub.

2. The device of claim 1 comprising limiting means for defining a height of said interior cavity to provide a desired truncated conical final form.

3. The device of claim 2 wherein said limiting means comprises said blank being severable substantially along another of said plurality of planes substantially parallel to and spaced from said one of said plurality of planes to form an open occlusal aspect of said core form having a cross-sectional size less than that of said gingival aspect of said core form.

4. The device of claim 2 wherein said limiting means comprises a conical insert receivable in the apical end of said blank, said insert being sized to limit the height of said interior cavity.

5. The device of claim 4 comprising a conical insert blank which is severable substantially along a plane substantially normal to its apical axis to produce said conical insert of a desired size for the tooth being restored.

6. The device of claim 1 wherein said blank is made of a thin flexible material.

7. The device of claim 6 wherein said blank has facial, lingual and proximal sides, and said facial and lingual sides at said gingival aspect are festooned with a contour corresponding generally to the cervical line of the tooth being restored.

8. The device of claim 7 wherein said blank is capable of being squeezed with the proximal sides being urged towards one another and then severable when in such squeezed state to form said festooned gingival aspect.

9. The device of claim 2 wherein said limiting means comprises an apex stop for attachment to said core form whereby the same serves as a handle for said core form.

10. The device of claim 9 wherein said core form may be embedded in said apex stop to attach the same thereto.

11. The device of claim 1 wherein said sidewall has a thickness of about 0.025 cm. to about 0.03 cm.

12. The device of claim 11 wherein said blank is about 2.1 cm. long and has a greatest diameter of about 1.2 cm.

13. The device of any one of the claims 1-8 wherein said sidewall has facial, lingual and proximal sides and said facial and lingual sides are, respectively, slightly longitudinally convex and concave.

14. The device of claim 1 wherein said sidewall has facial, lingual and proximal sides and said facial and lingual sides are, respectively, slightly longitudinally convex and concave, and at least one of said facial and lingual sides has a raised limiting ridge running longitudinally therealong for engaging the opposing tooth to facilitate proper spacing of the core form therefrom.

15. A multisize core form blank which may be sized to produce a core form for any one of a plurality of sizes of tooth stubs in the restoration of badly decayed or damaged teeth, said blank comprising a hollow generally conical body having a larger diameter base end, a small diameter apex end and a converging continuous sidewall extending from said base end to said apex end with facial, lingual and interproximal sides defining an interior cavity adapted to receive a hardenable composition and being severable substantially along any one of a plurality of planes substantially normal to the longitudinal axis of said body to produce a core form having an open gingival aspect opposite said apex end with cross-sectional size and shape to surround and conform to the tooth stub of such any one size.

16. A method of preparing a core for a crown on the remaining stub of a tooth, comprising the steps of:
a. preparing the tooth for receiving the core,
b. providing a dental device in the form of a thin walled, flexible, hollow generally conical blank having continuous converging sidewalls defining an interior cavity adapted to receive and to shape hardenable material,
c. severing the blank substantially along a plane substantially normal to the apical axis thereof to produce a core form having an open gingival aspect and a cross-sectional shape and size adapted for surrounding and conforming to the tooth stub,
d. filling the core form with a hardenable material,
e. locating the core form filled with hardenable material over the tooth stub with the gingival aspect thereof surrounding and conforming to the tooth stub,
f. allowing the material to harden, and
g. removing the core form from the tooth stub and hardened material.

17. The method of claim 16 wherein said step of preparing comprises root canal treatment of the tooth stub, obturation of the root canal, and insertion of a sized post into a root canal.

18. The method of claim 17 wherein said step of preparing comprises embedding pins into the remaining tooth structure with the pins projecting into the space to be occupied by the core.

19. The method of claim 16 comprising the step of severing the blank substantially along another plane substantially normal to the apical axis to define an occlusal aspect on the core form.

20. The method of claim 19 comprising the step of attaching an apex stop against the core form at the occlusal end thereof and applying pressure to such apex stop to firmly seat the core form on the tooth stub.

21. The method of claim 20 wherein the core form is attached to the apex stop by embedding the same in the apex stop.

22. The method of claim 16 comprising the step of inserting a conical insert into the blank to limit the height of the interior cavity.

23. The method of claim 16 wherein the hardenable material is a restorative material and comprising the steps of finish grinding the restorative material after removal of the core form from the tooth stub.

24. The method of claim 17 wherein the hardened material and embedded post form a core pattern and comprising the steps of removing the core pattern, casting a core and post, and then reinserting and cementing the casting core and post into the tooth stub.

25. The method of claim 24 comprising the steps of providing an apex stop having an opening therein, securing the apex stop to the core form at the occlusal aspect thereof with the post projecting through the opening in the apex stop, applying pressure to the apex stop to seat the core form, and using the projecting portion of the post as a sprue during casting.

26. The method of claim 16 comprising the step of fitting and securing a crown to the core.

27. The method of claim 16 wherein the sidewall has facial, lingual and proximal sides and the facial and lingual sides are, respectively, slightly longitudinally convex and concave.

28. The method of claim 27 wherein at least one of the facial and lingual sides has a raised limiting ridge running longitudinally therealong, and comprising the step of using the limiting ridge to facilitate proper spacing of the core form from an opposing tooth.

29. The device of claim 1 wherein said blank includes index marking means for aiding the dentist in selecting said any one of a plurality of planes.

* * * * *